United States Patent [19]

DeBernardis et al.

[11] 4,269,858

[45] May 26, 1981

[54] ANTIHYPERTENSIVE METHOD

[75] Inventors: John F. DeBernardis, Lake Villa; John J. Kyncl, Lake Forest, both of Ill.

[73] Assignee: Abbott Laboratories, North Chicago, Ill.

[21] Appl. No.: 144,742

[22] Filed: Apr. 28, 1980

[51] Int. Cl.³ .......................................... A61K 31/135
[52] U.S. Cl. .................................................. 424/330
[58] Field of Search ......................................... 424/330

[56] References Cited

U.S. PATENT DOCUMENTS 4,067,904   1/1978   Comer et al. .................. 424/330 X

OTHER PUBLICATIONS

Cantacuzene et al., Science, 204, pp. 1217–1219, Jun. 15, 1979.

Kirk et al., J. Med. Chem., 1979, 22(12), 1493–1497.

Daly et al., J. Pharmacol. Exp. Ther., Mar. 1980, 212(3), 382–389.

Primary Examiner—Frank Cacciapaglia, Jr.
Attorney, Agent, or Firm—Paul D. Burgauer; Robert L. Niblack

[57] ABSTRACT

2-Fluoronorepinephrine has been found to have antihypertensive activity when orally administered to warm-blooded animals.

6 Claims, No Drawings

ANTIHYPERTENSIVE METHOD

BACKGROUND OF THE INVENTION

The compound used in the current invention is described by Kirk et al., J. Med. Chem., 1979, Vol. 22, No. 12, page 1493, as a nearly pure $\beta$-adrenergic agonist.

DETAILED DESCRIPTION OF THE INVENTION

It has been known from the above publication that 2-fluoronorepinephrine acts as a pure $\beta$-adrenergic agonist with no $\alpha$-adrenergic activity in an in vitro environment on isolated tissue. It has been found that certain compositions of this compound are orally active antihypertensives in warm-blooded animals. The present invention is thus directed to the process of reducing hypertension by orally administering to a hypertensive, warm-blooded animal an anti-hypertensively effective amounts of 2-fluoronorepinephrine.

The effective amount for lower animals is between 10 and 250 mg./kg., preferably 25-150 mg./kg. In higher warm-blooded animals, the effective dose is between 10 and 100 mg./kg. per day or 0.6-4.0 g. as a single or b.i.d. dose for an adult human. A practical single dose contains 0.5-2.0 g. of the drug.

A preferred oral composition therealong contains about 1-2.5 g. of 2-fluoronorepinephrine in a solid dosage form. This may be a capsule containing the named amount or said amount may be incorporated into a tablet, pill, or wafer. Tablets and the like are easily prepared with the usual excipients such as a lubricant, starch, coloring and/or flavoring agents, etc. A common method for making tablets comprises milling about one-half of 52 g. of cornstarch with 300 g. of 2-fluoronorepinephrine and 220 g. of calcium phosphate dibasic dihydrate. This blend is milled until homogeneous and passed through a 40-mesh screen. The remaining portion of the cornstarch is granulated with water, heated, mixed with the above drug blend in a hot air oven at 50° C. and sifted through a 16-mesh screen. These granules are then mixed with 16 g. of talcum powder, 4 g. of magnesium stearate and 0.8 g. of combined coloring and flavoring agents. The mixture is blended until it is homogeneous, passed through a 30-mesh screen, blended for another 15 minutes and compressed into tablets weighing about 600 mg., using a standard convex punch resulting in tablets of a hardness of 7-9 with each tablet containing 300 mg. of the drug. In similar fashion, tablets weighing 900 or 1500 mg. can be made containing 450 or 750 mg. of the drug, respectively.

The above drug can also be administered as a syrup, elixir or other liquid dosage form whereby the diluent contains the usual stabilizers, coloring and flavoring agents, buffers and the like. In these dosage forms, the drug is preferably provided in unit dosage fashion and may be incorporated into the liquid medium in the form of granules of no more than 100$\mu$ diameter. Granules of the above type may also be combined with the usual excipients for making chewable tablets. Chewable tablets or the liquid dosage forms are often preferred for pediatric or geriatric patients. Obviously, numerous wellknown pharmaceutically acceptable liquid or solid diluents or carriers may be used in conjunction with the above drug.

The action of the oral dosage with 2-fluoronorepinephrine is best demonstrated by reference to the following example which, however, is not intended to limit the invention in any form.

EXAMPLE

Adult genetic hypertensive rats are divided into groups of four. Blood pressure measurements are made with a photo-cell and occuluding cuff on the tail. The rats are placed in a warming box which has a constant temperature of 33° C. before measurements are made. The blood pressure is taken before and at various times after the drug is orally administered to the animals fasted for 16 hours before dosing. The results are shown in the following tables which report the blood pressure and heart rate of the control animal and the % change measured after drug administration.

TABLE

|  | 100 mg./kg. | | | | 30 mg./kg. | | | | 10 mg./kg. | | | |
|---|---|---|---|---|---|---|---|---|---|---|---|---|
| Blood Pressure | | | | | | | | | | | | |
| Control (mm/Hg) | 248 | 242 | 240 | 238 | 231 | 250 | 204 | 221 | 211 | 212 | 245 | 190 |
| After 1 hr. % | | | | | 1 | −15 | −11 | −6 | 6 | 7 | −4 | 0 |
| After 4 hrs. % | −40 | −40 | −31 | −34 | 1 | −37 | −26 | −22 | 5 | −2 | 1 | 10 |
| After 6 hrs. % | | | | | 3 | −38 | −30 | −24 | 0 | 1 | 1 | 3 |
| After 24 hrs. % | | | | | −1 | −22 | −1 | 1 | 0 | −4 | −6 | 3 |
| Heart Rate | | | | | | | | | | | | |
| Control (bt/min) | 340 | 340 | 300 | 320 | 340 | 400 | 280 | 440 | 280 | 360 | 300 | 320 |
| After 1 hr. % | | | | | 0 | 15 | 79 | −9 | 14 | 11 | 40 | 19 |
| After 4 hrs. % | 24 | −29 | 53 | 44 | 6 | 10 | 43 | −14 | 14 | 11 | 27 | 6 |
| After 6 hrs. % | | | | | 6 | 5 | 50 | −9 | 21 | 28 | 13 | 0 |
| After 24 hrs. % | | | | | −24 | −20 | 0 | −32 | 7 | −6 | 13 | −6 |

The effect of the 100 mg./kg. dose was measured only after about 4 hours; it shows pronounced blood pressure lowering effect in fasted rats. At 30 mg./kg. the drug is shown to be very active also, while at 10 mg./kg. the dosage produces only marginal effect. Similar results are also obtained in dogs. The effective antihypertensive dose in animals therefore starts at about 10 mg./kg. and usually a daily dose of 30-100 mg./kg. will be sufficient to maintain a reduced blood pressure. In larger animals, including humans, a daily dose of about one-third of the above amounts will usually produce the desired effect.

We claim:

1. The method of lowering elevated blood pressure in warm-blooded animals consisting essentially in orally administering to a hypertensive animal an antihypertensively effective amount of 2-fluoronorepinephrine.

2. The method of claim 1 wherein said 2-fluoronorepinephrine is administered in unit dosage form.

3. The method of claim 1 wherein said 2-fluoronorepinephrine is administered in a dosage form together with a pharmaceutically acceptable diluent.

4. The method of claim 3 wherein said dosage form is a solid.

5. The method of claim 4 wherein said dosage form is a tablet.

6. The method of claim 1 wherein said dosage amount is between 10 and 250 mg./kg.

* * * * *